United States Patent [19]

Boiarski et al.

[11] Patent Number: 4,612,926
[45] Date of Patent: Sep. 23, 1986

[54] DUAL-RANGE ASPIRATOR DEVICE

[75] Inventors: Anthony A. Boiarski, Columbus, Ohio; Barbara H. Fleck, Randolph, Vt.; Eugene J. Meierhoefer, Hackettstown, N.J.; Richard Razgaitis, Columbus, Ohio

[73] Assignee: Battelle Development Corporation, Columbus, Ohio

[21] Appl. No.: 786,554

[22] Filed: Oct. 11, 1985

Related U.S. Application Data

[63] Continuation-in-part of Ser. No. 659,937, Oct. 12, 1984, abandoned, which is a continuation-in-part of Ser. No. 515,828, Jul. 21, 1983, abandoned, which is a continuation-in-part of Ser. No. 401,263, Jul. 23, 1982, abandoned.

[51] Int. Cl.$^4$ .............................................. A61M 11/02
[52] U.S. Cl. ........................... 128/200.21; 128/205.11; 239/338; 417/180; 137/890; 137/893
[58] Field of Search ...................... 128/200.18, 200.21; 239/338, 438, 443, 447, 448, 449, 458, 581, 407; 417/180; 137/890, 892, 893; 261/DIG. 65, 78 A

[56] References Cited

U.S. PATENT DOCUMENTS

| | | | |
|---|---|---|---|
| 163,876 | 6/1875 | Little | 417/180 |
| 576,259 | 2/1897 | Diamond | 417/180 |
| 3,913,607 | 10/1975 | Price | 128/205.11 |
| 3,977,432 | 8/1976 | Vidal | 128/205.11 |
| 4,036,253 | 7/1977 | Fegan et al. | 128/205.11 |
| 4,036,919 | 7/1977 | Komendowski | 128/200.21 |
| 4,039,639 | 8/1977 | Kankel et al. | 128/200.21 |
| 4,190,046 | 2/1980 | Virag | 128/200.21 |
| 4,195,044 | 3/1980 | Miller | 128/200.21 |

Primary Examiner—Henry J. Recla
Attorney, Agent, or Firm—Barry S. Bissell

[57] ABSTRACT

An aspirator/nebulizer for use in inhalation therapy has dual oxygen nozzles extending into a cylindrical chamber into which air can be aspirated in a controlled manner via closable air holes. A 50 psig oxygen source can be diluted to atmospheric air to yield an oxygen/air mixture comprising less than 30% oxygen at the conventional patient flow rates of 30-60 liters per minute. The dual oxygen nozzles also allow pure oxygen to be delivered at rates of at least 40 liters per minute when such high flow rates of relatively pure oxygen are needed for short term therapy.

4 Claims, 7 Drawing Figures

DUAL-RANGE ASPIRATOR DEVICE

This application is a continuation-in-part of our co-pending application Ser. No. 659,937, filed Oct. 12, 1984 and now abandoned, which is a continuation-in-part of Ser. No. 06/515,828, filed July 21, 1983 and now abandoned, which is itself a continuation-in-part of our application Ser. No. 06/401,263, filed July 23, 1982 and now abandoned.

BACKGROUND OF THE INVENTION

Aspirators, which provide a gaseous mixture and air, and humidifiers or nebulizers, which provide moist oxygen/air mixtures containing liquid droplets, are commonly used in inhalation therapy. Nebulizers can be constructed so that the oxygen/air mixtures they produce contain droplets of controlled size, which can be used to carry medicament to a patient's lungs. A single apparatus can function as both an aspirator and a nebulizer; when an aspirator is used, no liquid is supplied to the apparatus, whereas when a nebulizer is required liquid is supplied.

Aspirators and nebulizers are conventionally designed so that the energy needed to supply oxygen/air mixtures under positive pressure to patients, and in the case of nebulizers to nebulize the liquid, comes from a pressurized source of oxygen. Oxygen from this source is diluted with air and (if necessary) laden with medicament in the nebulizer in such proportions as prescribed by a health care provider.

The requirements for aspirators and nebulizers for use in inhalation therapy are becoming increasingly stringent since, in the long-term treatment of respiratory patients with moist oxygen/air mixtures, there is a trend towards the use of such mixtures with lower oxygen concentrations. Whereas oxygen/air mixtures containing 35% oxygen were typically used in the recent past, mixtures containing less than 30% oxygen are now desired. As illustrated in FIG. 4 below, the amount of air required to dilute pure oxygen (the only concentrated form of oxygen normally available in health care facilities) to produce a final concentration of oxygen in the oxygen/air mixture below, say, 30% oxygen is quite large. For example, to dilute a 29% oxygen mixture down to 27% oxygen requires an increase in the amount of diluting air of about 30%. Most current aspirators and nebulizers are not capable of diluting an oxygen stream to below 30% oxygen at moderate flow rates because of the large volume of air required.

However, although mixtures containing less than 30% oxygen are preferred for long term treatment, short term treatment sometimes requires undiluted oxygen. For example, a patient recovering from surgery may require a high-oxygen mixture (or even 100% oxygen) to flush remaining anesthetic from the patient's body. (For convenience, the term "oxygen/air mixture" is used herein to include the extreme case in which the "mixture" comprises 100% oxygen.)

At the same time, it is desirable that the aspirator or nebulizer be capable of producing a total oxygen/air mixture flow rate of at least about 40 liters/minute at all available oxygen concentrations in the mixture. Normal breathing requires a considerably lower rate of gas flow, but a traumatic event may temporarily require a flow rate as high as 40 liters/minute. In the high-dilution situation (i.e. when the oxygen/air mixture contains approximately 30% oxygen) an oxygen flow rate of less than 15 liters/minute is sufficient to yield a 40 liters/minute oxygen/air mixture flow rate. At low or zero dilution (i.e. when the oxygen content in the oxygen/air mixture approaches or reaches 100%) the rate of flow of oxygen alone must of course attain 40 liters/minute. Conventional aspirators and nebulizers are not able to achieve an oxygen flow rate as high as 40 liters/minute in a single unit at such high concentrations of oxygen (although they can be linked together in parallel to achieve this high, oxygen flow rate).

Finally, aspirators and nebulizers should be designed so that the oxygen concentration in the oxygen/air mixture remains fairly constant even though the flow demand may change, and should also be designed so that they can be manufactured sufficiently cheaply to be disposable.

As indicated above, no prior art aspirator or nebulizer meets all the foregoing requirements, and accordingly this invention is to provide an aspirator (also usable as a nebulizer) which can meet all these demands.

SUMMARY OF THE INVENTION

It is an object of the invention to provide a device for diluting an oxygen stream with ambient air.

It is also an object of the invention to provide such dilution to below about 30% oxygen concentration at reasonable flow rates for inhalation therapy.

It is further an object to provide a low-cost disposable device which dilutes and adds moisture and optional medicament to the oxygen stream.

It is finally an object to provide a device which can supply oxygen at conventional flow rates for ordinary operation and at high flow rates whenever needed.

Accordingly, this invention provides an aspirator device for supplying up to at least about 40 liters/minute of an oxygen/air mixture having a selectable oxygen concentration of from less than about 30% up to 100%. The instant aspirator device comprises a body member having walls defining a generally cylindrical chamber and at least one air inlet extending through a wall of the chamber so that the air inlet communicates at one end with the atmosphere surrounding the body member and at the opposed end with the chamber. The walls of the body member also define a gas outlet adjacent one end of the chamber and through which gas can leave the chamber. The instant aspirator device also comprises an oxygen flow controller for admitting oxygen (provided from any convenient source, such as the 50 psig oxygen lines conventionally provided in hospitals and other health care facilities) as an oxygen stream into the chamber in the body member. In order to satisfy the wide range of oxygen flow requirements needed in practice, the oxygen flow controller of the instant aspirator device has a first nozzle having a first orifice opening into the chamber adjacent the end of the chamber remote from the gas outlet, this first orifice being disposed adjacent the air inlet and arranged to continuously deliver oxygen at a low flow rate into the cylindrical chamber substantially parallel to the axis of this chamber. The flow of oxygen from the first orifice into the chamber causes aspiration of air through the air inlet into the chamber, thereby forming the oxygen/air mixture within the chamber and causing this mixture to leave the chamber via the gas outlet thereof. The oxygen flow controller also comprises a second nozzle having a second orifice opening into the chamber at a level above the first orifice, and means for varying the rate of flow of oxygen through the second orifice, so that then the second orifice is opened, the rate of flow of oxygen into the chamber is increased. A deflector downstream of the second orifice is used to arrest the oxygen flow therethrough and direct it away from the oxygen stream through the first orifice. This greatly improves lift of liquid from the bottle by preventing interaction of the first and second streams. Finally, the instant aspirator device comprises a slip-ring closure surrounding the chamber and movable relative to the inner inlet so that the slip-ring closure can be disposed to leave open, partially close or fully close the air inlet, thereby controlling the rate of aspiration of air through the air inlet into the chamber and hence the concentration of oxygen in the oxygen/air mixture.

Desirably, the instant aspirator device is formed so that it can also be used as a nebulizer. For this purpose, a liquid bottle separate from the body member, oxygen flow controller and slip-ring closure is secured to the body member so that a first opening in the liquid bottle is disposed adjacent the gas outlet in the body member. Thus, the oxygen/air mixture leaving the chamber via the gas outlet will pass through the first opening into the liquid bottle. In addition to the liquid bottle, the nebulizer form of the instant aspirator device has a lift tube for delivering liquid from the bottle, this lift tube having at its one end a liquid inlet disposed within the bottle and at its opposed end a liquid outlet, and a liquid nozzle having a liquid inlet connected to the liquid outlet of the lift tube, an outlet orifice, and a liquid conduit connecting the liquid inlet of the nozzle to its outlet orifice. The liquid orifice of the liquid nozzle is disposed within the chamber adjacent the first orifice of the oxygen flow controller and between this first orifice and the gas outlet so that oxygen delivered by the first orifice of the oxygen flow controller into the chamber will flow past the liquid orifice of the liquid nozzle, thereby creating suction in the liquid nozzle, drawing liquid from the bottle via the lift tube and the liquid nozzle into a chamber, and incorporating the liquid in droplet form into the oxygen/air mixture. Obviously, the liquid bottle may contain sterile water and, optionally, a medicament.

DETAILED DESCRIPTION OF THE INVENTION

Figure 1:
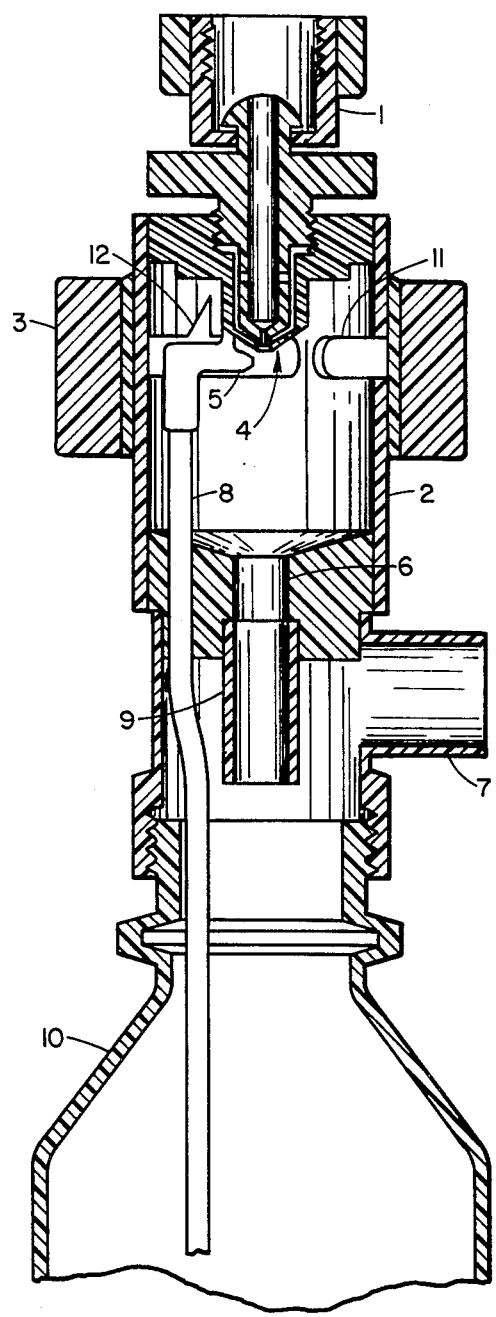
FIG. 1 is a vertical section through a first instant aspirator, shown mounted on a liquid bottle so as to act as a nebulizer.

The instant aspirator is designed so that a relatively low flow rate can be achieved using only the first nozzle of the oxygen flow controller, with the second nozzle closed, thereby producing a rate of oxygen supply which will be sufficient when relatively low oxygen content is required in the oxygen/air mixture. On the other hand, where high oxygen concentrations are needed, the second nozzle can be opened thereby producing a much greater total oxygen flow into the chamber. For convenience, the first orifice is sized to deliver a substantially sonic flow of oxygen at up to about 15 liters/minute from the oxygen source (such as a 50 psig oxygen supply line), while the second orifice is sized so that, when it is opened, the first and second orifices together will deliver a total of about 45 liters/minute of oxygen into the chamber. Other flow rates could have been chosen without departing from the spirit of the invention.

Two preferred forms of oxygen flow controller are used in the aspirator shown in the accompanying drawings. The first preferred form of oxygen controller (termed the "adjacent orifice" form and shown in FIG. 5) has first and second nozzles spaced from one another and valve means, preferably in the form of a stopcock, arranged to open and close the second orifice. The second preferred form of oxygen flow controller (termed the "concentric orifice form") has its first and second nozzles concentrically arranged and movable relative to one another so that the extent to which the first nozzle blocks the second orifice can be varied, thereby varying the rate of flow of oxygen through the second orifice.

It has been found that one important factor in producing sufficiently high dilution of the oxygen by the air aspirated into the cylindrical chamber is the distance between the first orifice of the oxygen flow controller and the gas outlet from the cylindrical chamber. In many prior art aspirators, the orifice by which oxygen enters the chamber is very close to the outlet from the chamber, so that air is only aspirated from the surroundings by the pressure difference caused by the oxygen flow. In contrast, in the instant aspirator it is desirable that the cylindrical chamber extend for a relatively long distance between the first orifice and the gas outlet to produce a so-called "open jet" condition. It is believed (although the invention is in no way limited to this belief) that in such an open jet, the air contacts the high velocity oxygen stream over a substantial distance, allowing the oxygen stream to accelerate the surrounding air by shear. This shearing, along with the pressure-induced aspiration, results in very efficient dilution of the oxygen stream, thereby enabling the aspirator to produce oxygen/air mixtures containing relatively low proportions of oxygen.

To provide the high dilutions particularly needed in health-care facilities (i.e. dilutions sufficient to produce oxygen/air mixtures containing no more than about 30% oxygen at oxygen flow rates of about 4–10 liters/minute), it has been found that the first orifice and the gas outlet from the cylindrical chamber should be separated by the distance related to the size of the entering oxygen stream i.e. to the size of the first orifice. To produce sufficient shearing of surrounding air and thus sufficient dilution, the distance between the first orifice and the gas outlet should at least equal about 50 times the diameter of the first orifice and preferably this ratio should be greater. Since in practice the diameter of the first orifice needs to approach 0.6 mm in order to produce an oxygen flow rate at sonic velocity of 6–15 liters/minute, the distance between the first orifice and the gas outlet should be at least 25 mm, and distances greater than about 30 mm are needed to achieve oxygen concentrations of below about 28%. In practice, separations of 25–50 mm are usually satisfactory, since in practice separations greater than about 50 mm tend to be difficult to achieve in conveniently sized aspirator devices. However, as described, when the instant aspirator is mounted on a liquid bottle, it may be possible to use the neck portion of the bottle as, in effect, an extension of the cylindrical chamber, thereby increasing the effective separation between the first orifice and the gas outlet.

FIG. 1 shows a first instant aspirator mounted on a liquid bottle 10 to form a nebulizer. The bottle 10 holds the liquid (with or without medicament) to be entrained in the oxygen/air mixture supplied to the patient. The aspirator comprises a body member 2 having a cylindrical chamber therein and an outlet 7 through which the moist oxygen/air mixture produced by the aspirator is supplied to the patient. Below the nozzle 7, the body member is threaded internally, and this internal thread engages a corresponding external pin on the neck of the bottle 10, thereby releasably securing the bottle 10 to the aspirator.

At the upper end of the body member is mounted an oxygen flow controller 4 which is capable of delivering an oxygen stream over a wide variety of flow rates into the cylindrical chamber within the body member. The flow controller 4 is connected through a source of pressurized oxygen (not shown) via a connector 1.

The cylindrical walls of the body member are pierced by air holes 11 which communicate at their outer ends with the atmosphere surrounding the aspirator and at their inner ends with the cylindrical chamber. A slip-ring closure 3 surrounds the body member adjacent the air holes 11 and can be slid parallel to the axis of the cylindrical chamber (i.e. vertically in FIG. 1) to leave open, partially close or fully close the air holes 11, thereby controlling the rate of aspiration of air through the air holes 11 into the cylindrical chamber. To provide greater sensitivity of adjustment of the air flow rate at low air flow rates (i.e. under low dilution conditions) a notch 12 is provided at the upper edge of one of the air holes 11, the slip-ring closure 3 being of course able to close the notch 12 as well as the holes 11. It should be noted that, in order to ensure good dilution of the oxygen entering the cylindrical chamber from the oxygen flow controller 4, the air holes 11 are arranged to lie adjacent the lower end of the flow controller 4 where the first and second orifices are located (as described in more detail below) so that the air holes 11 traverse the horizontal plane containing the lower end of the flow controller 4.

A liquid nozzle 5 is disposed within the cylindrical chamber and has an orifice which is disposed adjacent but below the lower end of the oxygen flow controller 4, and thus between the orifices in the tip of the controller 4 and the gas outlet (described below) at the lower end of the cylindrical chamber. Although not shown in FIG. 1, the liquid nozzle 5 has an orifice at its tip, and a liquid conduit extending through the nozzle to a liquid inlet at the opposed end of the liquid nozzle 5. This liquid inlet of the liquid nozzle 5 is connected to a liquid outlet at one end of a lift tube 8 which extends downwardly through the gas outlet at the bottom of the cylindrical chamber and out of the lower end of the body member into the bottle 10. The lower end of the lift tube 8 forms a liquid inlet which, when the bottle 10 is partially filled with water or other liquid, is immersed in this liquid. The oxygen flowing from the orifices at the tip of the controller 4 passes at a high rate past the orifice in liquid nozzle 5, thereby exerting a venturi and shearing action on liquid within the liquid nozzle 5, and causing liquid to be drawn from the bottle 10 up the lift tube 8 and through the liquid nozzle 5 into the cylindrical chamber, the liquid being nebulized by the high velocity oxygen stream.

At the lower end of the cylindrical chamber there is provided a downwardly-tapering frusto-conical section which joins the cylindrical chamber to a mixing nozzle 6 and an exit nozzle 9. The frusto-conical section, the mixing nozzle 6 and the exit nozzle 9 together constitute a gas outlet from the cylindrical chamber, this gas outlet directing the oxygen/air mixture formed within the cylindrical chamber downwardly into the bottle 10.

Figures 2, 4:
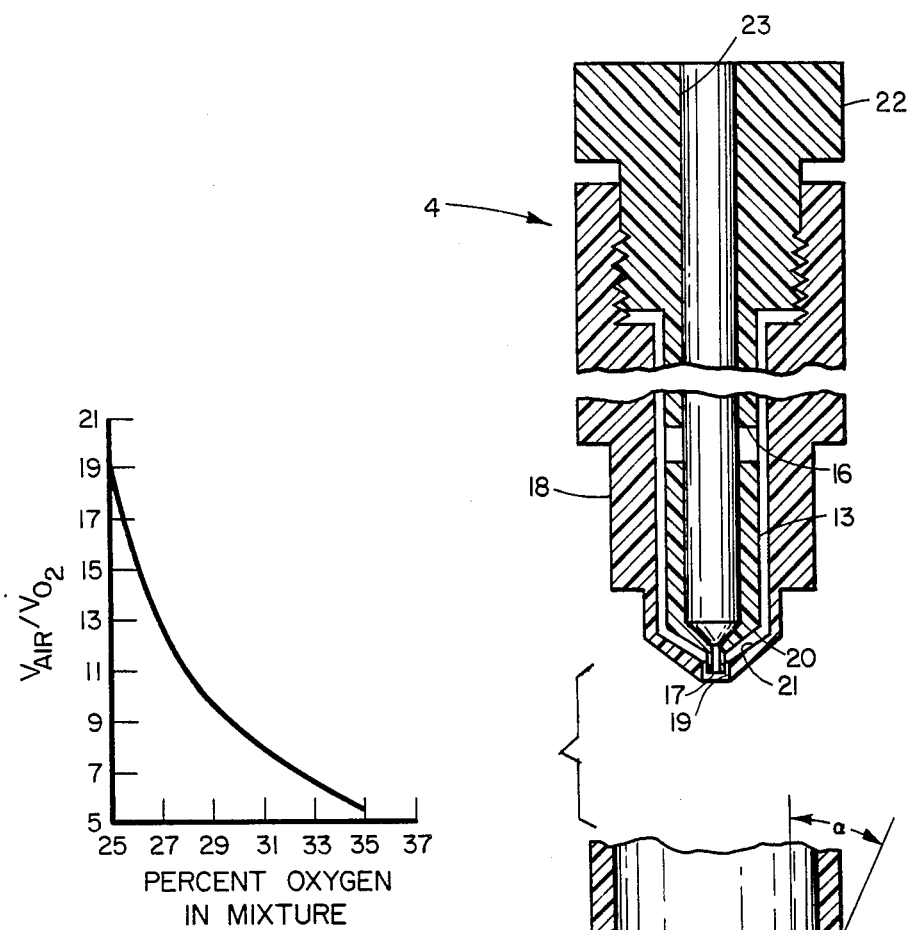
FIG. 2 shows an enlarged section through the oxygen flow controller shown in FIG. 1 and a section through an alternate form of the lower end of the body member of the aspirator which can be substituted for that shown in FIG. 1.
FIG. 4 is a graph showing the number of volumes of air needed to dilute a unit volume of oxygen to form an oxygen/air mixture having a given percentage of oxygen.

The flow controller 4 shown in FIG. 1 is shown in more detail in the upper part of FIG. 2. As shown in that figure, this flow controller 4 is of the "concentric orifice" type. The flow controller 4 comprises a first nozzle 13 comprising three separate cylindrical sections, namely an uppermost section 22, a central threaded section of smaller diameter than the section 22, and a lowermost section of smaller diameter than the central section. All three sections are coaxial and a channel 23, which is in fluid communication with the source of oxygen via the connector 1 (see FIG. 1) extends axially through all sections. Vents 16 extend radially through the lowermost section of the first nozzle 13, establishing fluid communication between the channel 23 and the exterior of the first nozzle 13. Also, at the lower end of the first nozzle 13, there is provided a downwardly-tapering frusto-conical section having an external surface 20 and a small cylindrical tip section bedding at its end a first, circular orifice 17, which is in fluid communication with the channel 23. As best seen from FIG. 1, the first orifice 17 is located on the axis of the cylindrical chamber. When the aspirator is connected to the oxygen source, oxygen flows continuously at substantially sonic velocity out of the first orifice 17, thereby sucking liquid out of the liquid nozzle 5 and nebulizing this liquid in the oxygen/air mixture in the manner already described. The first orifice 17 is sized so that, when connected to a 50 psig oxygen line, the conventional rate of flow of oxygen through the first orifice 17 during use will be in the range of 4–10 liters/minute. The vents 16 are substantially larger in cross-sectional area than the first orifice 17.

The flow controller 4 also comprises a second nozzle 18 which concentrically surrounds the first nozzle 13. The second nozzle 18 has four coaxial sections, namely an uppermost cylindrical section, a second cylindrical section of smaller diameter than the uppermost section, a third cylindrical section of smaller diameter than the second section, and a lowermost downwardly-tapering frusto-conical section. The upper part of the uppermost section of the second nozzle 18 is provided with an axial bore the cylindrical walls of which are threaded. The threaded wall of this axial bore is engaged with the thread provided on the central section of the first nozzle 13, so that the central section of the first nozzle is accommodated within the bore of the second nozzle 18.

From the lower end of this bore in the upper end of the second nozzle 18, a second axial bore of lesser diameter extends through the lower part of the uppermost section of the second nozzle 18 and through the second and third sections thereof. This second bore is slightly larger in diameter than the lowermost section of the first nozzle 13 which is accommodated therein. The lowermost frusto-conical section of the second nozzle 18 is hollow and accommodates the frusto-conical section of the first nozzle 13, the internal wall of this hollow frusto-conical section of the second nozzle being designated 21. A second orifice 19 passes axially through the lower end of the frusto-conical section of the second nozzle 18, the cylindrical section of the first nozzle adjacent the orifice 17 projecting into the orifice 19. As clearly shown in the cross-section in FIG. 2, the above described formation of the first and second nozzles leaves an annular chamber between the external surfaces at the lower end of the first nozzle and the internal surfaces of the second nozzle, thereby permitting oxygen to flow from the channel 23 through the vents 16 into this annular chamber. With the first and second nozzles in their relative positions shown in FIG. 2, oxygen entering this annular chamber can leave the second nozzle via the orifice 19. However, because of the engagement of their screw threads, the first and nozzles can be rotated relative to one another and it will readily be apparent to those skilled in the art that if the second nozzle is rotated relative to the first nozzle so as to lift the second nozzle relative to the first nozzle until the walls 20 and 21 come into contact with one another, escape of oxygen from the annular chamber via the orifice 19 will be prevented, thereby completely blocking the second orifice 19 and allowing only oxygen flows through the first orifice 17.

The second orifice 19 is sized so that when the second orifice 19 is fully open, the total oxygen flow through the first and second orifices will be at least about 45 liters/minute. Obviously, intermediate rates of oxygen flow can be produced by allowing the lower end of the first nozzle to partially block the orifice 19 thereby reducing the rate of oxygen flow therethrough. In practice, markings can be provided on the section 22 of the first nozzle, or on a suitable marker adjacent thereto, to show the approximate rate of flow of oxygen through the aspirator as a function of the position of the first nozzle 13.

Returning to FIG. 1, it will be seen that the mixing nozzle 6 terminates in an exit nozzle 9 which, in the embodiment of FIG. 1, has the form of a hollow cylinder. The mixing nozzle and exit nozzle are not essential features of the instant apparatus and need not be provided at all. If provided, it is desirable that the lower end of the exit nozzle 9 extend below the outlet 7 to prevent the moist oxygen/air mixture from being discharged directly out of the outlet 7. The exit nozzle need not have the hollow cylindrical form shown in FIG. 7. For example, the lower part of FIG. 2 shows an alternative form of mixing nozzle and exit nozzle having a frusto-conical entrance section 14, which has a much smaller apical angle than the corresponding frusto-conical section shown in FIG. 1, a mixing nozzle 6 and a frusto-conical diverging section 15, which replaces the hollow cylindrical exit nozzle 9 shown in FIG. 1. In the form of mixing nozzle and exit nozzle shown in the lower part of FIG. 2, the semi-apical angle (designated alpha) of the frusto-conical section 14 is conveniently about 60°–90°.

Figure 3:
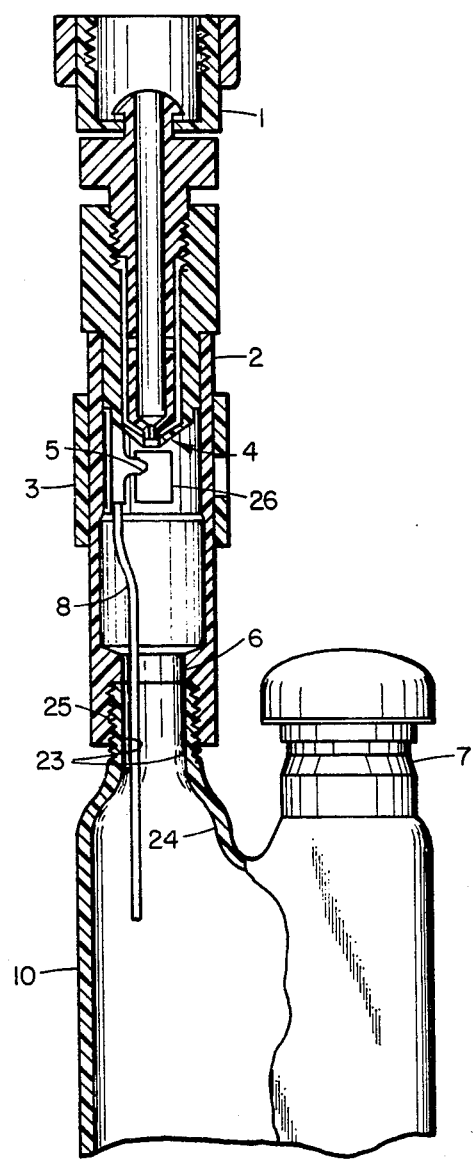
FIG. 3 is a vertical section, similar to that of FIG. 1, through a second instant aspirator shown mounted on a liquid bottle to form a nebulizer.

FIG. 3 shows a section through a second instant aspirator which is generally similar to that shown in FIG. 1 and which also uses the concentric nozzle form of oxygen flow controller. In the embodiment of the invention shown in FIG. 3, the air holes 26 are rectangular and the slip-ring closure 3, which has apertures passing therethrough, is arranged to rotate about the body member 2 so as to close, partially open or completely open the air holes 26.

In the apparatus shown in FIG. 3, the bottle has two separate openings therein. The first opening is surrounded by a neck having an external thread 23 thereon. This thread 23 can engage a corresponding thread 25 provided on the internal surface at the lower end of the body member 2, and the mixing nozzle 6 and the size of the adjacent neck of the bottle are arranged so that the internal opening within the neck acts as a direct continuation of the mixing nozzle 6, being cylindrical, of the same diameter as, and coaxial with, the mixing nozzle 6 within the body member 2. In the apparatus shown in FIG. 3, the lift tube passes down the mixing nozzle 6 into the interior of the bottle 10, rather than passing through the solid material surrounding the mixing nozzle, as in the embodiment of FIG. 1. The bottle 10 is provided with a second outlet 7 through which the moist oxygen/air mixture can leave the bottle and be fed to the patient. Obviously, the means by which the bottle is attached to the aspirator can be varied; for example, a bayonet mounting could be substituted for the screw thread shown in FIG. 3. It will be appreciated that the form of aspirator shown in FIG. 3, for use with a bottle having two openings, results in a simpler, less costly aspirator device to mold and fabricate.

Figure 5:
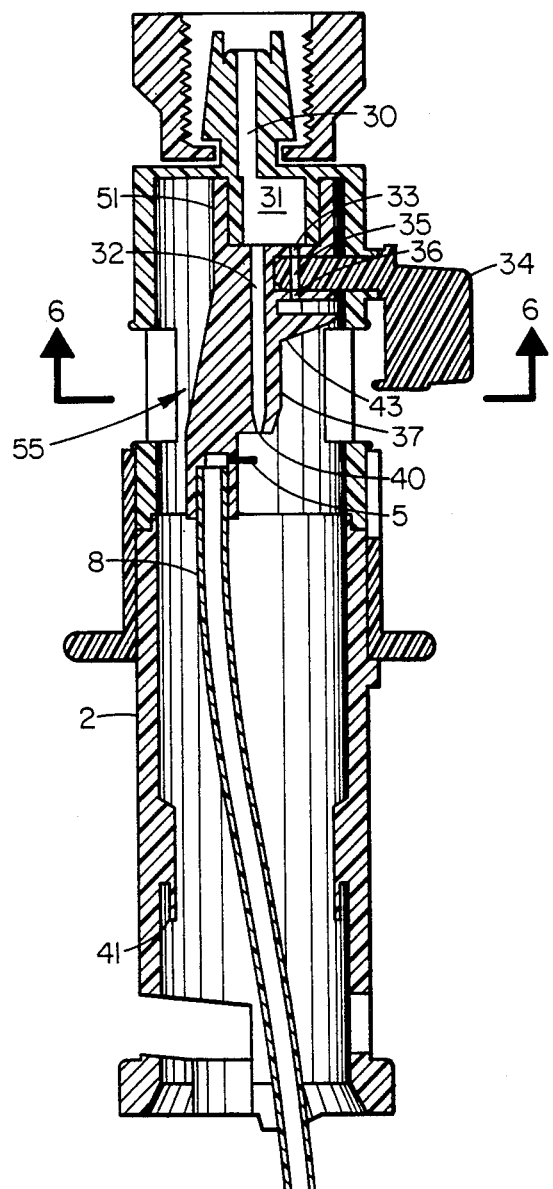
FIG. 5 is a vertical section, similar to those shown in FIGS. 1 and 3, through a third instant aspirator shown mounted on a liquid bottle to form a nebulizer.

The third instant aspirator, shown in FIG. 5, has an oxygen flow controller of the adjacent orifice type, but is otherwise generally similar to the aspirator device shown in FIG. 3. In the aspirator device shown in FIG. 5, pressurized oxygen enters the oxygen flow controller through a channel 30 and emerges into a chamber 31. From the chamber 31, the oxygen flows through a passageway 32 extending through a first nozzle 37 having a first orifice 40. When the channel 30 is connected to a 50 psig. oxygen supply, the first orifice 40 delivers oxygen at substantially sonic velocity, and at the rate of about 8 l/min., into a cylindrical chamber within body member 2. A liquid nozzle 5, connected to a lift tube 8, is positioned within the cylindrical chamber so that the oxygen emerging from the first orifice 40 will effect nebulizing of the liquid in the liquid nozzle 5.

To enable higher rates of oxygen flow to be achieved from the chamber 31 into the cylindrical chamber within the body member, the oxygen flow controller is provided with a second orifice comprising aligned bores 33 and 36. A stopcock 34 having a bore 35 extending therethrough is disposed between the bores 33 and 36 and is rotatable. In the position of the stopcock 34 shown in FIG. 5, the bore 35 is aligned with the bores 33 and 36 so that oxygen from the chamber 31 can pass through the bores 33, 35 and 36 against deflector 43 and into the cylindrical chamber in the body member, the lower end of the bore 36 thus acting as the second orifice of the oxygen flow controller. However, obviously by rotating the stopcock 34, the bore 35 can be moved out of alignment with the bores 33 and 36, thereby preventing oxygen flow through the bore 36 into the cylindrical chamber. The bores 33, 35 and 36 are sized so that, when the bore 35 is aligned with the bores 33 and 36, the total rate of oxygen flow through the two orifices into the cylindrical chamber is approximately 45 liters per minute.

The oxygen flow through the bores 33, 35 and 36 into the cylindrical chamber takes no part in the nebulization of liquid from the liquid nozzle 5. In fact, the deflector 43 is mounted immediately below the lower end of the bore 36 to deflect and reduce the downward velocity of the oxygen stream emerging from the bore 36 in order to ensure that this oxygen stream does not interfere with proper nebulization of the liquid from the liquid nozzle 5 by the oxygen stream emerging from the first orifice 40. The second orifice is located above the level of the first orifice. Were they at substantially the same level, the deflector would necessarily be in the cylindrical chamber within body member 2 downstream of the first orifice and would interfere with good aspiration of air by the oxygen.

The deflector 43 is therefore positioned above the level of the first orifice (and, of course, below the second orifice). Its function is to dissipate the very high energy of the second oxygen stream before it can divert or disrupt the first oxygen stream and affect its high nebulization efficiency. This energy dissipation results from reducing the downward velocity component of the oxygen stream from the second orifice from nearly sonic velocity (about 300 meters per second) to an average of less than about 5 meters per second. Besides being located between the two orifices, the deflector is preferably substantially horizontal (less than about 20° from being horizontal). It should be thin enough that it does not extend substantially below the level of the first orifice.

The deflector needs to be large enough to dissipate the oxygen stream but not so large that it prevents the flow of oxygen gently downward from the second orifice into the chamber to mix with the first oxygen stream, aspirated air and nebulized liquid. Since the oxygen stream emanating from the orifice diverges away from the orifice, the deflector should be of such size and shape, depending on its distance from the orifice, that it intercepts substantially the entire expanded oxygen stream. For example, for a separation of about 5 diameters of the oxygen orifice (about 6.5 mm), the minimum size of a preferred deflector would be about 1 diameter (or about 1.3 mm diameter). This 1:5 ratio appears to roughly predict the minimum deflector size for arbitrary separations.

Figure 6:
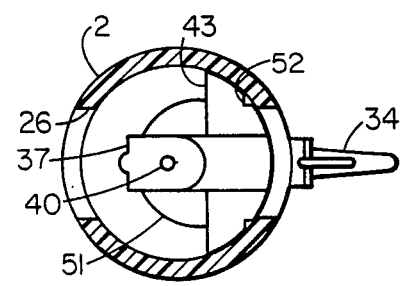
FIG. 6 is a horizontal section through the body of the device shown in FIG. 5 with exposure of the deflector plate.
Figure 7:
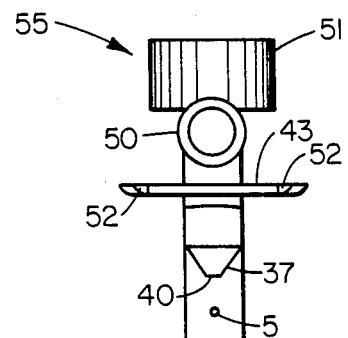
FIG. 7 is an elevation view of the molded nozzle and deflector subassembly.

In FIGS. 5, 6 and 7, the deflector is shown in its preferred form as a horizontal, thin, semicircular plate covering less than half of the chamber cross-sectional area. A typical separation distance of about 2 mm is shown. It is substantially larger on the "wings" than would be necessary to arrest the entire oxygen stream, but this is due to considerations of support and manufacturing efficiency. The deflector 43 (as seen best in FIG. 7) is molded integrally into a subassembly 55 with the first nozzle 37, a circular housing 50 containing bores 33 and 36 for the stopcock 34 and an annular connector 51 at the top for press fitting around the walls of chamber 31. Notches 52 are used as positioning means during assembly of the device.

In the aspirator device shown in FIG. 5, the mixing nozzle has been almost eliminated. From the lower end of the body member 2, an annular flange 41 extends inwardly and then downwardly to produce a relatively small reduction in the diameter of the cylindrical chamber; this flange 41 in effect defines the air outlet from the cylindrical chamber. The neck of a bottle (not shown in FIG. 5) is inserted into the lower end of the body member 2, being held therein by means of a bayonet fitting (a screw thread fitting may of course alternatively be used) so that the extreme upper end of the neck is accommodated in the groove formed between the lower side of the flange 41 and the cylindrical wall of the body member 2. Because of the relatively small projection of the flange 41 into the lower end of the cylindrical chamber within the body member, it will be appreciated that the cylindrical hollow interior of the neck can in effect act as a continuation of the cylindrical chamber within the body member, thereby allowing additional room for mixing and formation of any homogenous oxygen/air mixture. The lift tube 8 passes downwardly through the circular aperture within the flange 41 and the bottle. Like the bottle shown in FIG. 3, the bottle can be equipped with a second outlet through which the oxygen/air mixture is withdrawn and fed to the patient.

It will be apparent to those skilled in the art that, by slight modification of the design of the lower end of the body member 2 and the flange 41, the constriction introduced by the flange 41 in the aspirator device shown in FIG. 5 could be completely eliminated, so that the hollow interior of the neck 42 could constitute a direct continuation of the cylindrical chamber within the body member 2. In this case, the air outlet from the cylindrical chamber would be defined by the extreme lower end of the body member 2.

The inventors have found the following conditions to be generally preferred in delivering at least 40 l/min. of pure oxygen from a 50 psig oxygen source or in diluting it to a final air/oxygen mixture of less than 30% oxygen at delivery rates of about 30–60 liters/minute using the device of FIG. 3.

TABLE 1

| Small Oxygen Orifice (circular) | |
|---|---|
| Diameter | 0.4–0.6 mm (calculated to give near sonic flow) |
| $O_2$ flow rate | 4–10 l/min |
| Large Oxygen Orifice (annular) | |
| Diameters | 2.5 mm I.D. × 2.75 mm OD annulus |
| $O_2$ flow rate (total with small orifice) | 40–45 l/min |
| Mixing Nozzle | |
| Diameter | 8–10 mm |
| Converging entrance angle ($\alpha$) | 60–90° |
| Throat length | 1–4 cm |
| Diverging exit angle ($\beta$) | 10–40° |
| Distance (L) from $O_2$ Orifices to Mixing Nozzle | 2.5–4 cm |

The surprising effect of the distance (L) between the orifices of the oxygen flow controller and the gas outlet from the mixing chamber in an apparatus using the form of gas outlet/mixing nozzle shown in FIG. 2 is illustrated below in Table 2. The second, annular orifice was closed and the first, circular orifice had a diameter of 0.6 mm and was connected to a 50 psig oxygen source to deliver 6 liters per minute of oxygen. The gas outlet/mixing nozzle had a 60° convergence angle on the leading face, a 25.4 mm long throat and a 20° diverging angle on the trailing face. The distance (L) between the first orifice and the gas outlet at the lower end of the cylindrical chamber was varied while the oxygen concentration in the gas mixture and the backpressure in the bottle were recorded.

TABLE 2

| Distance "L" (mm) | Oxygen Concentration in gas mixture (%) | Mixture Backpressure (mm H₂O) |
| --- | --- | --- |
| 15.9 | 29.4 | 4.8 |
| 19.0 | 28.9 | 6.35 |
| 22.2 | 28.1 | 7.6 |
| 25.4 | 27.7 | 8.35 |
| 28.6 | 27.3 | 9.15 |
| 31.7 | 27.0 | 9.9 |
| 34.9 | 27.0 | 10.3 |
| 38.1 | 26.9 | 10.8 |
| 41.3 | 26.8 | 11.3 |

As shown, the oxygen concentration may be decreased significantly (and thus the quantity of air aspirated into the cylindrical chamber increased significantly) by increasing the separation between the orifices of the oxygen flow controller and the gas outlet from the cylindrical chamber i.e. by increasing the length of the cylindrical chamber. For example, increasing the separation from 25.4 mm to 44.4 mm decreases the oxygen concentration in the final mixture about 1%, from 27.7 to 26.7% oxygen. Although this reduction in oxygen concentration may appear small, it will be seen from FIG. 4 that to effect this small decrease in oxygen concentration the volume ratio of air to oxygen must be increased from less than 12:1 to about 14:1. Thus, it will be seen that the increased separation between the oxygen orifices and the gas outlet from the cylindrical chamber (a so-called open-jet arrangement) is extremely effective in aspirating air into the cylindrical chamber. Comparison of the data in Table 2 with the graph in FIG. 4 shows that the air aspiration is substantially improved when the orifices are separated by at least 25 mm from the gas outlet. Hence this is the preferred separation in an aspirator device within the parameters tested in this example. In general, the optimum separation may be somewhat affected by both the oxygen orifice and gas outlet sizes, but the available hospital oxygen pressure and the delivery rates required closely dictate the sizes chosen in this example. This the preferred 25 mm minimum separation is virtually an absolute limitation for proper dilution in use of the instant aspirator/nebulizer device in hospital application, while a distance of about 50 mm represents a practical maximum preferred separation.

It will be apparent to those skilled in the art that numerous changes and improvements can be made in the preferred embodiments of the invention described above without departing from the scope of the invention. Accordingly, the whole of the foregoing description is to be construed in an illustrative and not in a limitative sense, the scope of the invention being defined solely by the appended claims.

We claim:

1. An aspirator device for supplying up to at least about 40 liters/minute of an oxygen/air mixture having a selectable oxygen concentration of from less than about 30% up to 100%, said device comprising:
   (A) a body member having walls defining a generally cylindrical chamber and at least one air inlet extending through a wall of said chamber, said air inlet communicating at one end with the atmosphere surrounding said body member and at the opposed end with said chamber, said walls of said body member also defining a gas outlet adjacent one end of said chamber and through which gas can leave said chamber;
   (B) an oxygen flow controller for admitting oxygen as an oxygen stream into said chamber, said oxygen flow controller comprising a first nozzle having a first orifice opening into said chamber remote from said gas outlet, said first orifice being disposed adjacent said air inlet and arranged to continuously deliver an oxygen stream at a low flow rate into said cylindrical chamber subtantially parallel to the axis thereof so as to aspirate air through said air inlet into said cylindrical chamber, thereby forming said oxygen/air mixture within said chamber and causing said mixture to leave said chamber via said gas outlet, said oxygen flow controller further comprising a separate second nozzle adjacent said first nozzle and having a second orifice, and valve means for varying the rate of flow of oxygen through said second orifice, said second orifice opening into said chamber so that, when it is open, the rate of flow of oxygen into said chamber is increased;
   (C) a slip-ring closure surrounding said chamber and moveable relative to said air inlet so that said slip-ring closure can be disposed to leave open, partially close or fully close said air inlet, thereby controlling the rate of aspiration of air through said air inlet into said chamber and hence the concentration of oxygen in said oxygen/air mixture;
   (D) a liquid bottle separate from said integers (A), (B) and (C) and having first and second openings, said liquid bottle being secured to said body member so that said first opening is disposed adjacent said gas outlet in said body member so that said oxygen/air mixture leaving said chamber via said gas outlet will pass through said first opening into said liquid bottle and will leave said liquid bottle via said second opening;
   (E) a lift tube for delivering liquid from said bottle, said lift tube having at its one end a liquid inlet disposed within said bottle and at its opposed end a liquid outlet;
   (F) a liquid nozzle having a liquid inlet connected to said liquid outlet of said lift tube, an outlet orifice and walls defining a liquid conduit connecting said liquid inlet of said nozzle to said outlet orifice thereof, said liquid orifice being disposed within said chamber adjacent said first orifice of said oxygen flow controller and between said first orifice and said gas outlet, such that said oxygen stream delivered by said first orifice of said oxygen flow controller into said chamber will flow past said liquid orifice of said liquid nozzle, thereby creating suction in said liquid nozzle, drawing liquid from said bottle via said lift tube and said liquid nozzle in said chamber, and incorporating the liquid in droplet form into said oxygen/air mixture; and
   (G) deflector means downstream of said second orifice for directing the oxygen flow therethrough away from said oxygen stream delivered by said first orifice such that said oxygen stream delivered by said first orifice is not diverted from drawing liquid from said bottle via said lift tube and said liquid nozzle.

2. An aspirator device according to claim 1 wherein said valve means is a stopcock for varying the oxygen flow through said second nozzle.

3. An aspirator device according to claim 1 wherein said first orifice and said gas outlet are separated by a distance of about 25 to about 50 mm.

4. An aspirator device according to claim 1 wherein said first nozzle delivers oxygen at near sonic velocity.

* * * * *